US011170001B2

(12) United States Patent
Rickert et al.

(10) Patent No.: US 11,170,001 B2
(45) Date of Patent: Nov. 9, 2021

(54) METHOD AND SYSTEM FOR PROCESSING DATA STREAMS

(71) Applicant: CorTec GmbH, Freiburg (DE)

(72) Inventors: Jörn Rickert, Freiburg (DE); Christian Stolle, Freiburg (DE); Jörg Sebastian Fischer, Teningen (DE); Martin Schüttler, Emmendingen (DE)

(73) Assignee: CorTec GmbH, Freiburg (DE)

( * ) Notice: Subject to any disclaimer, the term of this patent is extended or adjusted under 35 U.S.C. 154(b) by 518 days.

(21) Appl. No.: 15/829,221

(22) Filed: Dec. 1, 2017

(65) Prior Publication Data

US 2018/0102960 A1 Apr. 12, 2018

Related U.S. Application Data

(63) Continuation of application No. PCT/EP2016/062664, filed on Jun. 3, 2016.

(30) Foreign Application Priority Data

Jun. 3, 2015 (DE) ...................... 10 2015 108 859.2

(51) Int. Cl.
*G06F 16/20* (2019.01)
*G06F 16/2455* (2019.01)
(Continued)

(52) U.S. Cl.
CPC ........ *G06F 16/24568* (2019.01); *G06F 16/22* (2019.01); *G16H 40/63* (2018.01); *G16H 40/40* (2018.01)

(58) Field of Classification Search
None
See application file for complete search history.

(56) References Cited

U.S. PATENT DOCUMENTS

| 2006/0107325 A1* | 5/2006 | Kanestrom ......... G06F 21/6209 726/26 |
| 2007/0213786 A1* | 9/2007 | Sackellares .......... A61B 5/0476 607/45 |

(Continued)

FOREIGN PATENT DOCUMENTS

| WO | 2007058950 A2 | 5/2007 |
| WO | 2011124996 A1 | 10/2011 |

OTHER PUBLICATIONS

Xiong et al., Analysis of Distributed Consensus Time Synchronization with Gaussian Delay over Wireless Sensor Networks, 2009, EURASIP Journal on Wireless Communications and Networking [retrieved on Feb. 27, 2020], Retrieved from the Internet:< URL: https://dl.acm.org/doi/10.1155/2009/528161 >. (Year: 2009).*

(Continued)

*Primary Examiner* — Kristopher Andersen
(74) *Attorney, Agent, or Firm* — Myers Wolin, LLC

(57) ABSTRACT

A computer-implemented method of processing data streams is provided, the method comprising the following steps: receiving a number of data streams, at least one data stream thereof being representative of at least one physiologic signal of a patient sensed by a predetermined sensor device, and receiving at least one time stamp information, each time stamp information being associated with a respective data stream, the time stamp information being representative of the point in time of associating the time stamp information with the respective data stream, and associating a respective time shift information with each time stamp information, the time shift information being representative of a delay between a point in time of sensing the at least one signal by the predetermined sensor device and the point in time of associating the time stamp information with the data stream representative of the at least one signal.

12 Claims, 5 Drawing Sheets

(51) Int. Cl.
    *G06F 16/22*     (2019.01)
    *G16H 40/63*     (2018.01)
    *G16H 40/40*     (2018.01)
    *G16H 40/60*     (2018.01)

(56) References Cited

U.S. PATENT DOCUMENTS

| | | |
|---|---|---|
| 2009/0070266 A1 | 3/2009 | Shah et al. |
| 2010/0274303 A1 | 10/2010 | Bukhman |
| 2012/0290266 A1 | 11/2012 | Jain et al. |
| 2013/0178727 A1 | 7/2013 | Hayter et al. |

OTHER PUBLICATIONS

International Search Report, dated Aug. 26, 2016, for corresponding International Application No. PCT/EP2016/062664.
German Examination Report, dated Feb. 5, 2016, for corresponding International Application 10 2015 108 859.2 with an English translation.

\* cited by examiner

METHOD AND SYSTEM FOR PROCESSING DATA STREAMS

CROSS REFERENCE TO RELATED APPLICATIONS

This application is a continuation of International Application No. PCT/EP2016/062664, filed on Jun. 3, 2016, which claims priority to German Application No. 10 2015 108 859.2, filed Jun. 3, 2015, the contents of each of which are incorporated by reference herein.

TECHNICAL FIELD

The present invention relates to a method and a system for processing data streams, and in particular for processing data streams captured by neural implants and other sensor devices placed in or on a patient's body.

BACKGROUND

Most neuroprosthetic devices do not adapt their therapeutic parameters such as stimulation strength (current or voltage), stimulation frequency or stimulation pulse width over time. The devices are programmed once by physicians to work with the same parameters over and over. Only when the patient visits into the clinic, the physicians can change the parameters. A few very new devices do adapt their parameters—but only on one input measured by the device at the same time. Neither do they take into account input from other devices nor from history. Likewise, current devices have no or very limited capability to store data measured by the device.

One reason is that there is no system available where data acquired with one sensor device can be meaningfully combined with data acquired with one or more further sensors.

SUMMARY

It is an object of the present invention to provide methods and systems which alleviate at least partially these problems. This object may be addressed by the methods and systems and computer-readable storage media according to the claims.

Thus, the invention as defined in the claims is a method and system for recording data of implants that can be combined with other parameters recorded simultaneously and to use this data for analysis and/or adaptation of therapeutic parameters and/or for use as information in other therapies.

The method and system according to the disclosure can be used for temporally aligning the sensed data streams with high precision, typically in an order of magnitude of one or more milliseconds, into one data set, and for using this data set for adaptation of therapeutic parameters and/or for research e.g., for research data mining over multiple data sets, in other therapies or more.

BRIEF DESCRIPTION OF THE DRAWINGS

The invention is described by reference to the drawing, in which.

DETAILED DESCRIPTION

Figure 1:
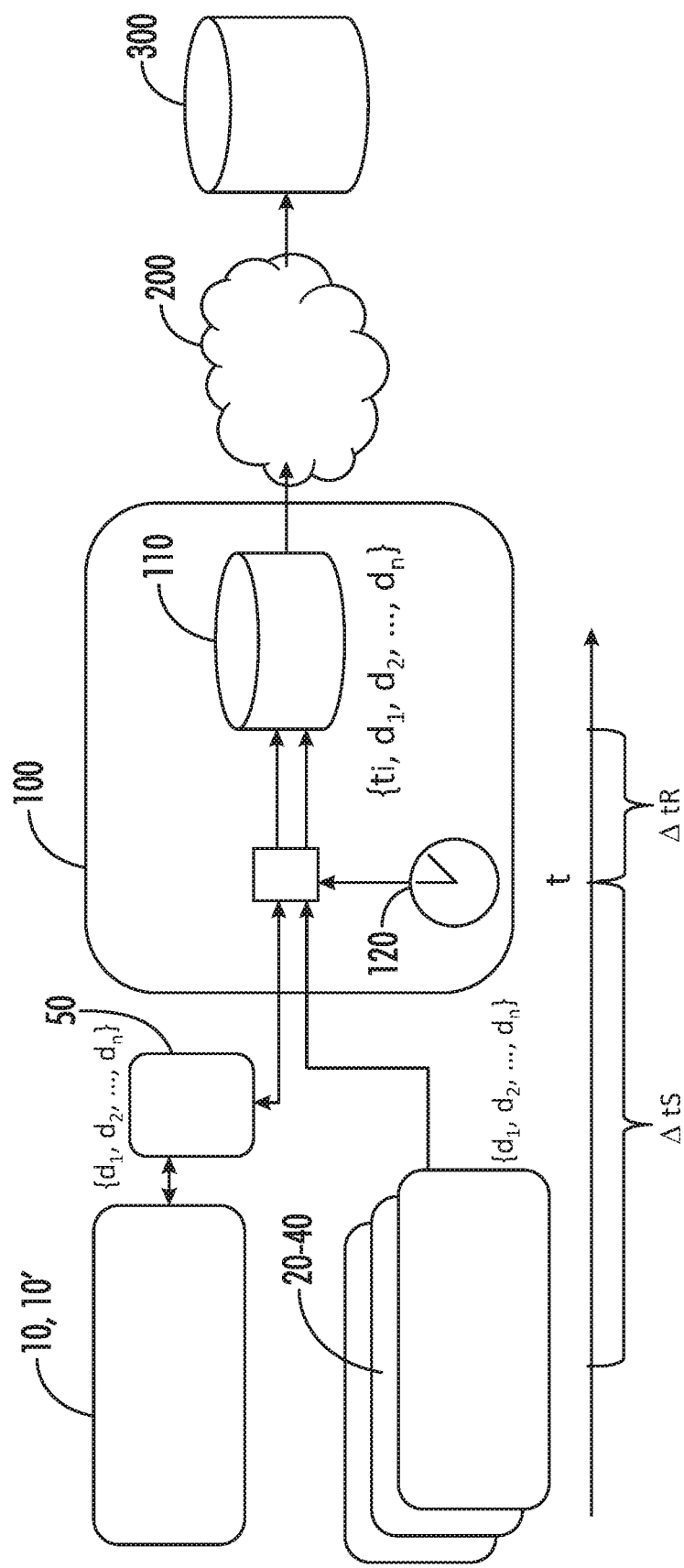
FIG. 1 is a scheme illustrating the data acquisition flow according to an embodiment of the invention.

The embodiment of FIG. 1 is a configuration where data originating from a patient is sensed, recorded, and further processed. As shown in FIG. 1, one or more neural electrode implants 10 are connected to an implantable control unit 50, which in turn is coupled with a body-external, portable-external, portable processing device 100. Further sensors 20-40 are present which are also coupled with the body-external, portable processing device 100. The neural implant(s) 10 and the further sensors 20-40 sense, e.g., neural signals, and other parameters from inside or outside human body. The sensed signals are converted into data streams and transmitted to the body-external, portable processing device 100 for further processing. Implantable control unit 50 is arranged in the data flow between the neural implant(s) 10 (and the further sensors 20-40) and the body-external, portable processing device 100 for reasons of space and accessibility. A neural implant 10 will in general not offer sufficient space for control electronics of the neural implant(s) 10 and for communication electronics to the outside of the human body.

More precisely, body-external, portable processing device 100 comprises a temporal storage 110 for at least temporal recording data streams $\{d_1, d_2, \ldots, d_n\}$, a time reference 120 for generating time stamps t and processing means for associating the data streams $\{d_1, d_2, \ldots, d_n\}$ with the time stamps t. That is, each of the data streams $\{d_1, d_2, \ldots, d_n\}$ representing the signals is recorded along with a time stamp information which is generated just at the time of actually recording the respective data stream.

Thus, the implant control unit 50 and the sensors 20-40 relay their signals in the form of data streams $\{d_1, d_2, \ldots, d_n\}$ to the body-external, portable processing device 100. The body-external, portable processing device 100 is a body-external device that can be carried by the patient. It comprises the time reference 120 which is used to generate sufficiently precise time stamps t (e.g., with precision in the order of one or more microseconds) and a temporal storage 110 (e.g., a sufficiently large hard disc or flash disc). When a data stream arrives at the body-external, portable processing device 100, a time stamp t is generated and assigned to this data stream and both are stored in the temporal storage 110. When a connection via a data transportation medium 200 (e.g., internet or local area network) to a database 300 is possible, the data from the temporal storage 110 (i.e., the data streams along with their time stamps) is transferred to the database 300. For the database 300, there are several configurations possible. E.g., the database can be a database server in a server farm/cloud or a computer at the patient's home.

Depending on the nature of the signals (or parameters) to be sensed, neural electrode implant(s) 10 and sensors 20-40 can be: For invasive physiological parameters, electrodes for recording electrical activity (voltage, current) from the brain or individual nerves, sensors for sensing of electrochemical gradients in order to identify concentrations of biomolecules, sensors for pH or blood glucose. For noninvasive physiological parameters, EMG, heart rate, skin conductivity, body movements (accelerometers), blood pressure.

Exemplary other non-physiological parameters to be sensed by sensors outside human body 20-40 are GPS position, environment parameters such as temperature, noise/sound (in Decibels), lightning level, weather. Some or all of the sensors 20-40 may be integrated within the body-external, portable processing device 100.

Neural electrode implant 10 may be a combined sensor and stimulation implant, i.e., it may function as a device for sensing neuronal signals, and as a device for applying stimulation impulses (signals) to the neuronal system.

Sensing neuronal activity and applying neuronal impulses may also be performed individually by separate neural electrode implants. Then, at least two neural electrode implants 10 are provided, one implant 10 for sensing neuronal activity, and one implant 10' for applying stimulation impulses (signals).

Invasive actuators can be: Electrodes for electrical stimulation of the brain or individual nerves, actuators for applying medication, noninvasive actuator can be: Hand-/arm or speech prostheses, warning sensors sending alarms to hospitals/physician or to the patient himself.

The time reference 120 can be a radio-controlled clock, a timeserver regularly updating system time running on electronics, GPS, network time protocol (internet used by PCs/electronics to update their time automatically), and other means which deliver exact coordinated universal time information (UTC). The precision should be preferably in an order of magnitude of milliseconds as mentioned above, and more preferably in an order of 2-4 ms, in particular cases it should be 1 ms. This corresponds to the order of magnitude of the sampling rate of the neural signals.

Taking as the time stamp t the point in time of storing the respective data stream in the temporal storage 110 of the body-external, portable processing device 100, this may not be sufficiently exact for the purpose of synchronizing the data streams with data streams captured with other sensors, and/or for triggering stimulation pulses. The reason for that is that there may be substantial delays between actually sensing the signals by the implant 10, or by the other sensors 20-40, and storing them in the temporal storage 110 of the body-external, portable processing device 100, where the time stamp t is generated. This is in particular true for neuronal signals, which are extremely short and may have spectral portions and/or frequencies in the order of magnitude of some kHz up to some MHz.

Thus, according to the disclosure, the exact time synchronization may take into account for each neural implant 10, sensor devices 20-40, and processing device 100, the delay $\Delta t_S$ between the point in time of actual sensing the signal by the neural implant 10, sensor devices 20-40, and the point in time t when a time stamp was generated and associated with the data stream representing the sensed signal, i.e., the point in time when the data stream is actually going to be recorded by the body-external, portable processing device 100. In general, for each sensor 10, 20-40, the respective delays $\Delta t_S$ will exhibit a respective predefined probability distribution. From the knowledge of the respective probability distribution, the delay $\Delta t_S$ for a particular sensor can be derived. For example, a sensing device 10, 20-40 which exhibits a Gaussian distribution for its delay $\Delta t_S$ can be modeled by its mean delay and the variance of the delay. Given these parameters, the most likely point in time of the event occurrence (represented by the sensed signal) can be calculated from the stored time stamp t.

Further, the delay $\Delta t_R$ of the recording means of the body-external, portable processing device 100 itself may be taken into account (if there is any). Then, the delay $\Delta t_S$ between sensing the signal (representing the event) and recording the data stream as well as the delay $\Delta t_R$ of the recording means of the time-processing device 100 itself is taken into account, i.e., by directly subtracting the difference in the average delay between time-processing device 100 and sensor signal from the stored time stamp t associated with the data stream: $t'=t-(\Delta t_S+\Delta t_R)$. Other computations of the delays $\Delta t_S$, $\Delta t_R$ may be performed if the time reference points and/or the signs of the delays are different.

As a minimum information, average delays should be known. All information about the delays of particular implants 10, sensors 20-40, implantable control unit 50, and processing devices 100, respectively, is preferably stored in a product specification database, which may preferably be external to the processing device 100 and database 300.

The data streams thus temporally aligned (i.e., synchronized with each other) may be used for adaptation and update of therapeutic parameters: First of all, the therapeutic parameters of the neural implant 10 and its implantable control unit 50 can be updated based on the data stored in the database 300: Analysis of the database will send via the data transportation medium 200 (same way backwards as the data upload described above) an update to the actuators (implants) and sensors 10-40 and the control unit 50 where the algorithm for the computation of actuator activity based on the recorded sensor activity will be updated. For example, neural activity in particular is known to change or adapt over time because of learning, habituation and other factors of neuronal plasticity. To take this into account, therapeutic parameters need to be adapted likewise over time.

In another mode, this update runs via the patient's private network device 200, where the patient can control the update manually (i.e. for testing etc.). Every change to the parameter set of a sensor 20-40 or an actuator (implant) 10 is also stored in the database 300 and is annotated with a respective time stamp. This way, changes to sensors 20-40 and actuators 10 are also traceable.

Moreover, the data stored in the database 300 can be used by physicians for diagnostics. In one version, the data of a certain set of parameters in a time-window of interest can be made available to the physician.

In an advanced version, diagnostic data acquired and recorded by a physician with his own technical equipment, clinical staff, or by the patient himself, is labeled with a time stamp t too, and uploaded to and stored in the database 300, whereby the time stamps are corrected as described above. Conversely, the physician may use the time-stamped data he recorded with his equipment directly, without uploading to the database 300, in combination with the data recorded by the body-external, portable recording unit 100 and uploaded to the database 300.

As an example, a patient wearing a neuroprosthetic device (along with a body-external, portable processing device 100) comes to an eye specialist where a physician presents different stimuli to the patient and also records his pupil contraction. The stimuli and data relating to the pupil contractions are stored along with their recording delays and precise time stamps. The data can then be uploaded via an interface to the database 300 where it is synchronized with the brain activity of the patient acquired by the patient's neuroprosthetic device and sent to the database 300 via body-external, portable processing device 100. The patient's eye diagnostics can then be carried out by the physician as if having recorded the patient's brain activity in parallel by himself.

Another example relates to research data mining: Data streams from multiple patients can be processed, together with the data streams from other sensors, for new insights into the relations between neurological processes and these sensor data streams. Data sets can be exported, either in raw form or in preprocessed form (e.g., up- or down-sampled or converted in another file format).

For each type of data stream (e.g., neuronal data or electrocardiogram), the events represented by the data streams and the time stamps are stored in the database 300. For each device type, the parameters of the probability distribution for the delay are also stored in a product database.

For the sake of safe identification and security of data, a unique pseudonym may be assigned to each patient. In order to protect the private data of patients, each patient's personal data (e.g., name and address) is stored separately and encrypted together with its pseudonym. The patient's sensor data is stored unencrypted and associated only with the patient's pseudonym.

Access to the database 300 may be allowed only via encryption protocols that ensure privacy and ensure the authenticity of the person that wants to access the database.

The transmission of data via data transportation medium may be encrypted, whereas the strength of the encryption depends on the type of data that is transported and the transportation medium.

The security/encryption level is chosen by patient or her physician depending on the clinical need and the protection of privacy. Partial information maybe uploaded online continuously for clinical needs, for example critical safety parameters (heartrate etc.).

Figure 2:
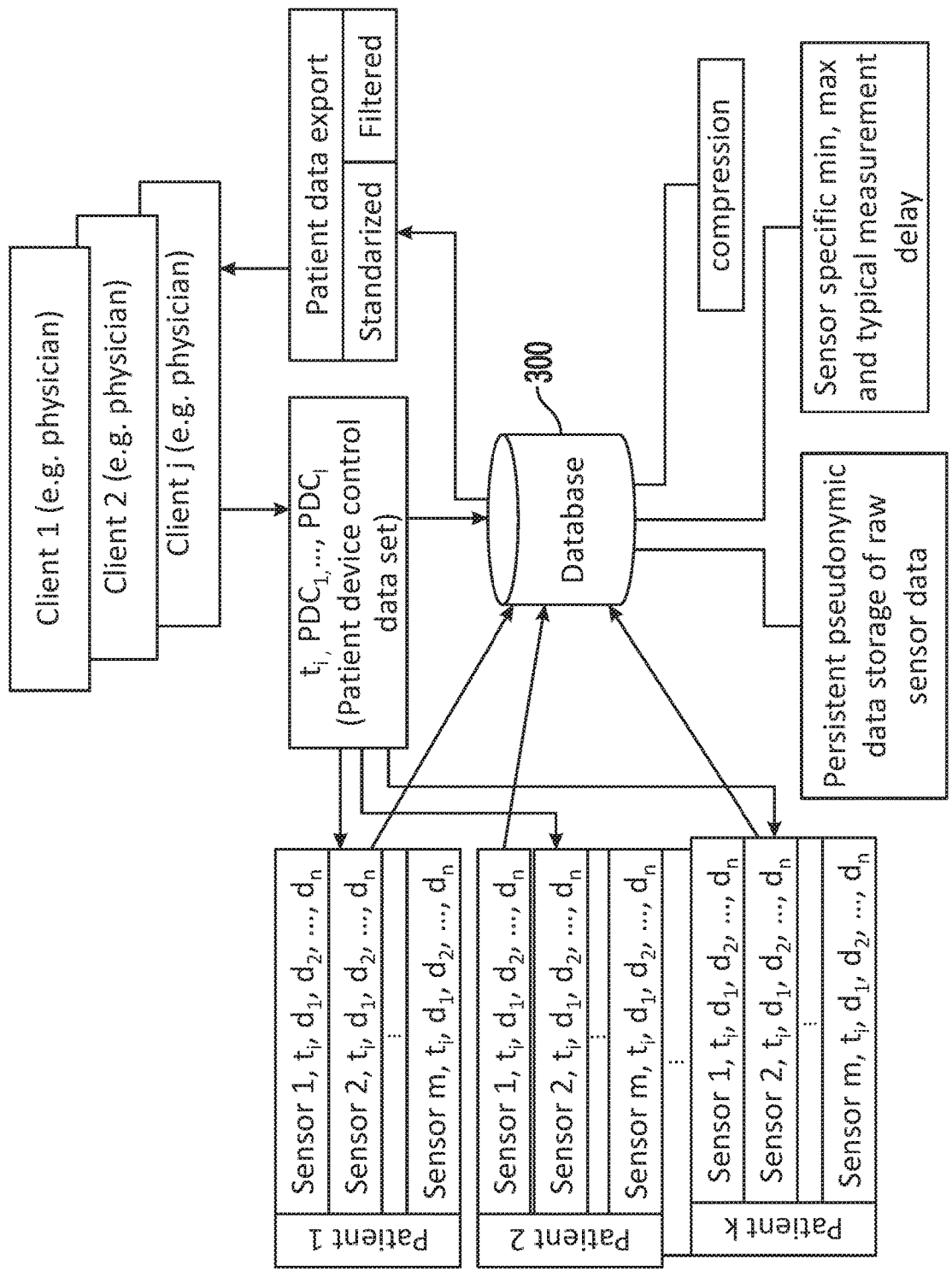
FIG. 2 is a scheme illustrating a relationship of time information and database content.

FIG. 2 is a scheme illustrating the relation of time information and database 300 content in a larger context. As can be seen from FIG. 2, the database 300 may store data streams from several patients 1, 2, . . . k. Each patient may be equipped with several sensor devices 1, 2 . . . , m, each sensor device sensing signals or parameters and producing data streams therefrom. As described before, each data stream $\{d_1, d_2, \ldots, d_n\}$ is representative of at least one event (represented by a signal). With each data stream $\{d_1, d_2, \ldots, d_n\}$, a respective time stamp $t_i$ is associated. The time stamp $t_i$ (i being the index for the $i^{th}$ sensed event) is generated and associated by patient's body-external, portable processing device 100. Data streams along with their time stamps $t_i$ are transmitted from there to the database 300 (upon availability of a transfer medium 200) and stored there.

All or a number of the data streams $\{d_1, d_2, \ldots, d_n\}$ as well as control data for the sensors 10, 20-40, implant control unit 50, and actuators relating to one patient may be referred to as a patient data and device control data set (PDC). The data stored in database 300 may be exported in a standardized format and may be made available to clients 1, 2, . . . , j (e.g., physicians) for diagnosis. On the other hand, some clients may have direct access to particular or all PDC of the database 300. The data may be compressed for capacity or transmission reasons.

Sensor specific measurement delays $\Delta t_S$ of the sensor devices 10, 20-40, and delays $\Delta t_R$ of the recording means of processing device 100 may be accessed on a product specification database. This database bay be external to the database 300 where the measurement data is stored. On the other hand, the delays $\Delta t_S$, $\Delta t_R$ pertinent to particular sensor devices 10, 20-40, and processing devices, respectively, may be kept available in database 300, too.

The database 300 may also store raw data, i.e., data as delivered by the sensors, which is not processed in any way.

The data collected by the processing device 100 can be used in several ways. First, the data can be pre-processed and then sent to the corresponding database 300 for further processing or analysis purposes as described above.

Second, the collected data can be transmitted to a stimulation unit, which is formed by implantable control unit 50 and stimulation implant, i.e., implantable electrode 10'. It may be connected via a real-time capable bus system (e.g., a CAN Bus) or via a wireless link with the processing device 100. The sensor data is sent to the stimulation device at the rate of its recording. The stimulation device comprises the implant control unit 50 and the implant 10', whereby the controller is implemented by a control algorithm (e.g., neural network, fuzzy logic, etc.). The actuator part comprises electrodes, signal generation, etc. The controller processes the sensor data according to its current parameter set, generates the corresponding set values for the actuator part of the system, and feeds them back to the actuator part of the system. In this way, a closed-loop stimulation system is provided.

All parts of the closed loop system (e.g., processing device, control algorithms) are configured using a vector of control parameters. Sensors may change their data acquisition rate or filter settings based on these parameters. Control algorithms are defined or adjusted by these parameters (e.g. edge weights in artificial neural networks, PID parameters, etc.).

Based on the analysis of measured data at the data base side (e.g. by a physician) the parameter vector can be updated via the transport medium 200. The parameter vector update can either be triggered by a poll request initialized by the measurement device or by a database-side push. The database push is triggered by inserting a new control set into the database 300.

As safety measure, the parameter space can be restricted to a safe subspace. The control vector is verified as to whether it is within the boundaries of the safe subspace before it is applied. Only if the vector is safe it is transferred to the corresponding device parts. The next measurement data will then be processed and generate control outputs according to the new parameter vector. Changes in the parameter vector are recorded along with the current time stamp t in the database 300. The safety subspace can be defined by the physician e.g. during an ambulatory treatment session.

Figure 3:
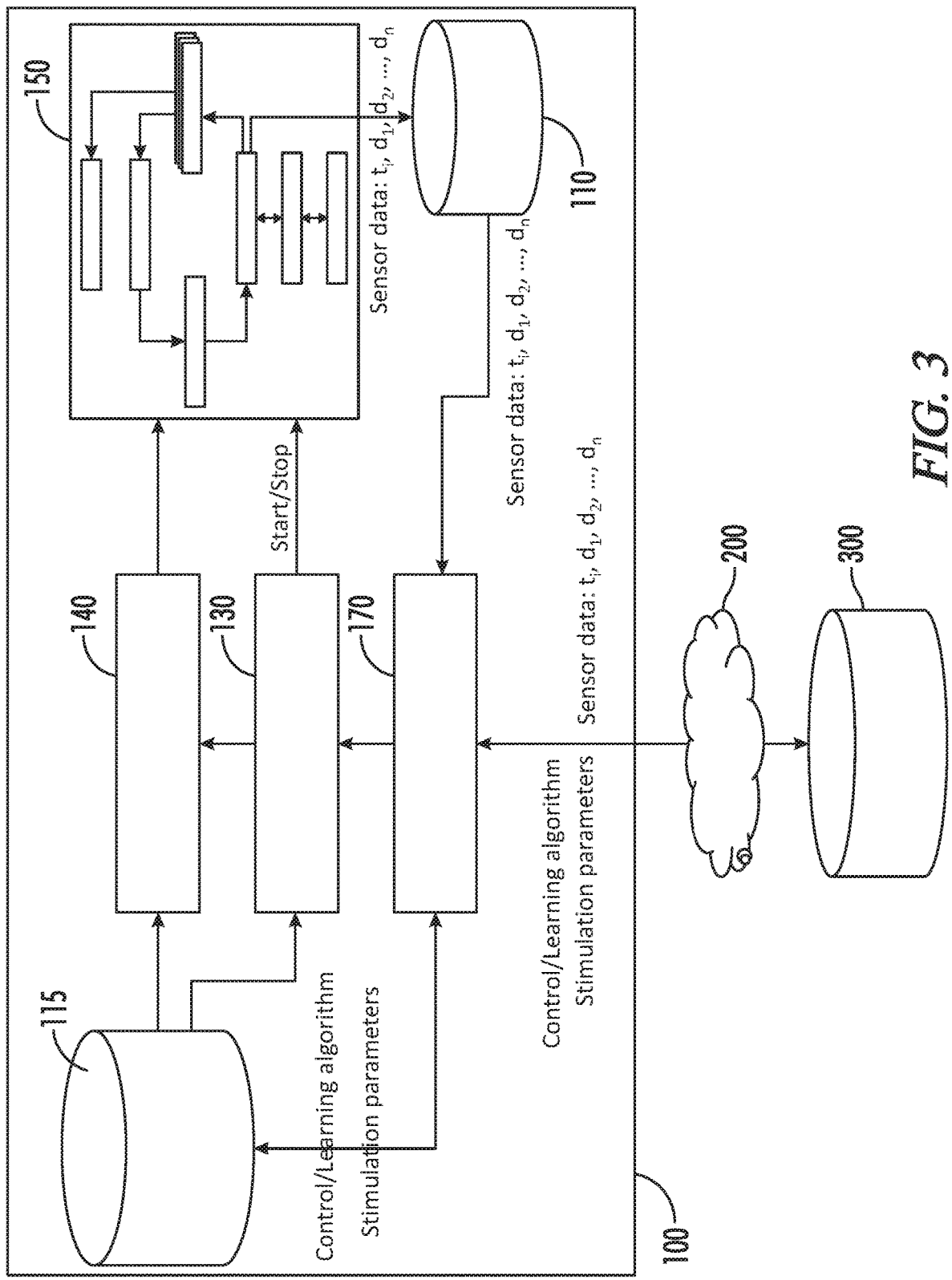
FIG. 3 is a scheme of the device system architecture with a central database connection.

The system architecture of the body-external, portable processing device 100 including the main software components is described in FIG. 3. All parts of the body-external, portable processing device 100 (including the plugin pipeline) store their data in the temporal storage 110. The processing is performed by a CPU. An operating system which is capable of running multiple threads is installed.

The system made up of multiple parts. One part is the configuration database 115, which is located preferably in the temporal storage (e.g., hard drive, flash drive, etc.) 110. This database 115 contains general application information including, what kinds of plugins (see below) need to be loaded, and what kinds of configuration parameters should be applied. Part of these parameters is the control vector as well as the possibly different safe parameter subspace for the patient and the physician.

The pipeline manager 130 uses the plugin pipeline builder 140 to create and initialize the plugin pipeline 150 based on the parameters in the configuration database 115. In addition, it controls start/stop of the measurement loop.

Figure 4:
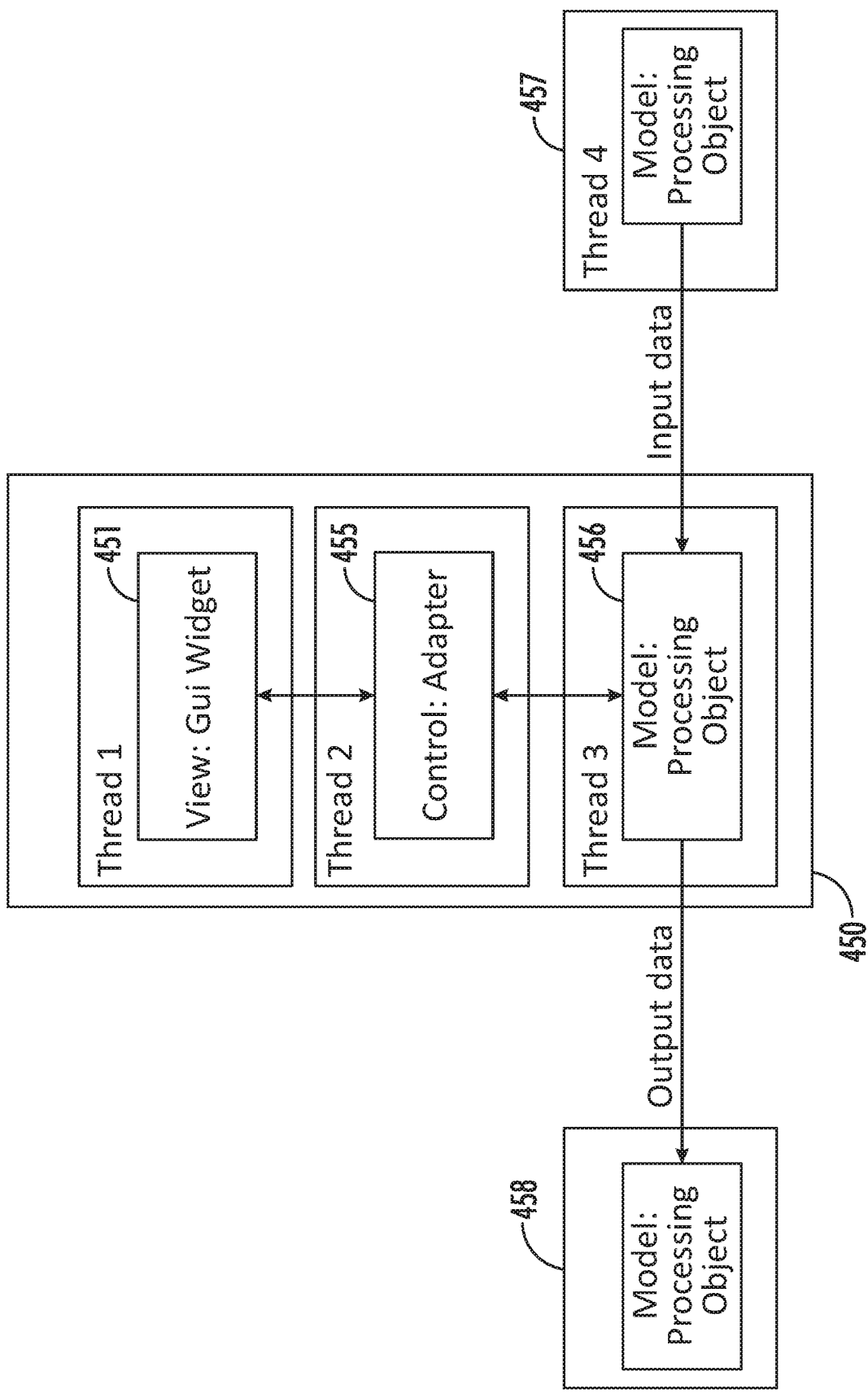
FIG. 4 is a model view of the control architecture of a single plugin.

The plugin pipeline 150 is made up of several plugins 450. FIG. 4 is a block diagram of a single plugin. The individual plugins are designed by the model view control software design pattern. Therefore, the graphical user interface (GUI) of each plugin 450 may only access the model via the controller (i.e. adapter) 455. The adapter 455 modifies the model (i.e. processing object) 456, which in turn tells the adapter 455 about model changes. These changes are then sent back to the view 451. Therefore, the system's main GUI consists of a view container containing the individual plugins' views. New data is pushed to the processing object by its predecessor, locally processed and then passed to the successor. Lazy copying is applied. Therefore, the data is only copied if the data needs to be changed. Every plugin part is running in its own thread. Processing objects 456, 457, 458 can be connected if the type of the data of two consecutive objects is of the same type. A connection graph is stored as part of the configuration database 115. The connection graph represents the plugins and their interconnections, wherein the nodes of the graph correspond to the plugins, and edges of the graph correspond to the connections between the plugins. Thus, based on this graph the individual plugins are connected to each other for implementing a particular hardware/software system on the body-external, portable processing device 100.

Figure 5:
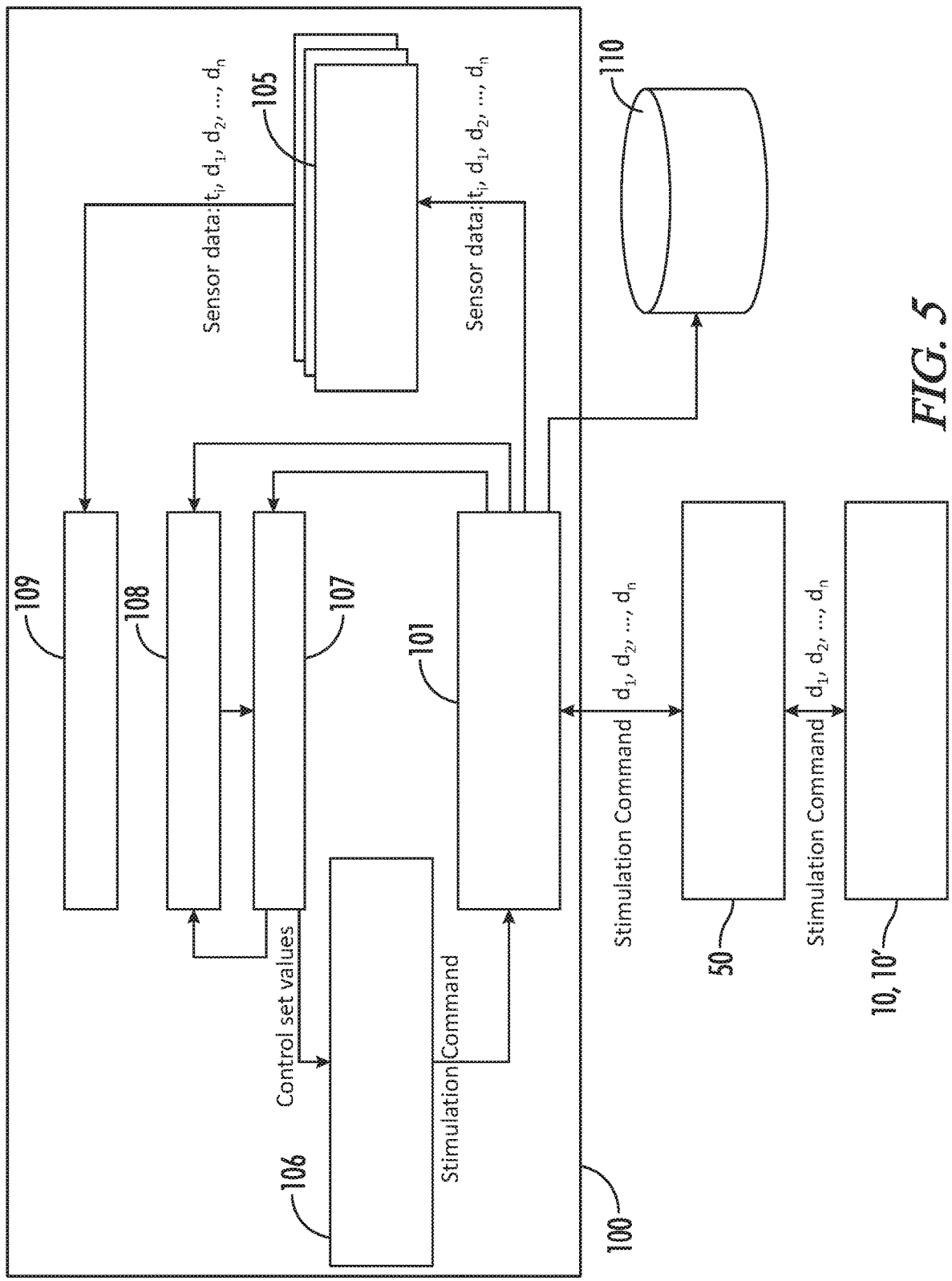
FIG. 5 is a view on the plugin pipeline for closed-loop applications.

The flexible and scalable plugin system can be configured such that a closed-loop system is formed (see FIG. 5). There is one hardware communication plugin 101 for every sensor 10, 20-40 connected to the system. For example, FIG. 3 illustrates the connection to a neural implant 10 for neural signals. Stimulation commands $\{d_1, d_2, \ldots, d_n\}$ are passed by the plugin to the implant control unit 50, which is connected to the body-external, portable processing device 100. The implant control unit 50 in turn is connected to neural implant 10. The neural signal recordings are sent via the implant control unit 50 back to the hardware communication plugin 101.

This sensor data is sent to four different locations. First, it is extended by its time stamp t and stored to the temporal storage 110. This temporal storage 110 is preferably (but not necessarily) located on the same persistent drive as the configuration database 115. For visualization the sensor data is processed by possibly multiple preprocessing plugins 105 (e.g. notch filters, etc.). The result of this processing is sent to a visualization plugin 109, which plots the current sensor readings. The sensor data from the hardware communication plugin 101 can also be sent to a control algorithm plugin 107 and to the parameter learning algorithm plugin 108.

The purpose of the control algorithm plugin 107 is to generate stimulation set values, which correspond to the data read. The control set is influenced by the current control parameter vector, which may vary depending on the control algorithm in use.

The optional parameter learning algorithm plugin 108 starts with the control parameter set provided in the configuration database 115. Then, based on the sensor data and the output of the control algorithm plugin 107 it generates modifications of the control parameters if necessary. Both the control algorithm plugin as well as the learning algorithm may locally store several sensor readings in order to provide the means of an integrated mechanism for control.

The stimulation generator plugin 106 generates stimulation commands from the set values and sends them to back to the hardware communication plugin 101, which closes the control loop. It should be noted that there may be more than one kind of sensor 10 involved, which may all sent their data to either one or multiple control/learn algorithm pairs (cascade control).

The communication manager 170 (refer to FIG. 5) connects the temporal storage 110 through the transport medium 200 with a central database 300 if the connection is available and intended. The communication manager 170 ensures that all sensor data collected since the last synchronization is transferred to the central database 300. In turn, it pulls any configuration updates to the body-external, portable processing device 100. The configuration updates (e.g. control/learning algorithm, control parameter vectors, etc.) are first evaluated for correctness and safety. If the data is sound it is stored into the configuration database 115, and the pipeline manager is informed about these updates. The pipeline manager performs the required pipeline changes (e.g. replace control and learning algorithm, change control parameter vector).

As an example, cross-correlation of sensor activity and recording after stimulation or other measures of effectiveness can be used to determine optimal weights for each sensor of the closed-loop algorithm.

As a further example, the body-external, portable processing device 100 itself may run online or offline learning algorithms for adjusting the stimulation parameters. This is achieved by providing each sensor data stream and control algorithm output as input of the learning algorithm. The output can change control parameters "on the fly" (e.g., applied to a fuzzy logic controller with an artificial neural network for online control parameter learning). The advantage of this online learning approach is that it can handle daily fluctuations of the patient's condition.

Another example is to record environment for safety or adaptation of stimulation parameters with respect to safety, for example to increase stimulation to a more effective level when driving a car. Hereto, a determination is needed whether the person is actually driving a car. This may be done by combining a GPS sensor, and a body-external, portable movement sensor which detects movements of e.g., the hands or arms of the person. Thus, if the GPS sensor detects a movement with a higher speed, and the body-external, portable movement sensor detects movements according to a typical driver's profile, the system may increase (or suggest to the person increasing) the strength and/or frequency of the stimulation pulses.

Moreover, the exactly time-tagged data streams may be used for calibrating the system, by recording the system's impulse response, which is approximated by recording the neural activities/sensor activities in response to the strongest possible single pulse stimulation/actuator activity applied. As the stimulation pulse for safety reasons is limited in strength to the maximal stimulation (voltage or current) allowed, this characterization is carried out repeatedly, typically 10-25 times, and the results are averaged until only minor differences occur and statistical significance of the model is reached.

The model of the system generated by this characterization then can be used to predict sensor activities in response to certain stimulation or actuator patterns. This can be used twofold: On the one hand, to define the stimulation/actuator activities that produce sensor activity(ies) indicative for a desired patient state, for example low oscillations in the beta-range in certain brain regions, i.e., the motor cortex or in the nucleus subthalamicus. And on the other hand, to prevent stimulation parameters that achieve undesired neural activities or brain states, for example activity that leads to increased oscillations in the beta range in certain brain regions, activity that might lead to seizures, invoke uncontrolled movements.

The data streams may be stored in the data base 300 in different ways. For each patient, the data streams relating to different parameter may be stored in a two-dimensional matrix:

time×parameters, separate for each patient.

For several patients, in particular if the data streams of several patients correspond to each other, the data streams may be stored in three-dimensional matrix:

time×parameters×patient.

The delays (between the sensing the signal relating to an event by the sensor device 10, 20-40 and the recording of the signal by the processing device 100, often a few hundred ms) may be subtracted before alignment in the database 300. This subtraction may either occur upon storage in the temporary processing device 100 or upon storage at the database 300. Of course, if diagnosis and/or adaptation of parameters is done at a later time, the alignment may be done only at that later occasion.

The invention claimed is:

1. A computer-implemented method of processing data streams by a body-external, portable processing device, the method comprising the following steps:

receiving a number of data streams, at least one data stream thereof being representative of at least one physiologic signal of a patient sensed by a predetermined sensor device, the predetermined sensor device being a neural implant, and the physiologic signal representing an electrical activity of brain or nerves, and generating at least one time stamp information at the body-external, portable processing device, the at least one time stamp information being based on a time reference comprised by the body-external, portable processing device, each time stamp information being associated with a respective data stream of the number of data streams, each time stamp information being representative of the point in time of associating the time stamp information with the respective data stream, recording, in a body-external temporal storage device, the at least one data stream and at least one time stamp information associated thereto, and associating a respective time shift information with each time stamp information, and recording the time shift information associated with the time stamp information in the body-external temporal storage device, the time shift information being based at least on the corresponding predetermined sensor device associated with the corresponding data stream, and representative of a delay between a point in time of sensing the at least one signal by the predetermined sensor device and the point in time of associating the time stamp information with the data stream representative of the at least one signal, wherein information about the delay is retrieved from a product specification database comprising information relating to at least the predetermined sensor device, and wherein the product specification database comprises entries for a plurality of sensor devices, each entry comprising information about delays associated with the corresponding sensor devices, and wherein different sensor devices of the plurality of sensor devices have different delay information.

2. The method of claim 1, further comprising transmitting the recorded at least one data stream, and the respective time stamp information to a database, and storing the at least one data stream, the time stamp information, and the associated time shift information in the database.

3. The method of claim 2, wherein transmitting to and storing in the database is done when a data transmission medium is available to the body-external, portable processing device.

4. The method of claim 1, wherein at least one data stream of the number of data streams is representative of at least one patient's body-external signal sensed by a predetermined sensor device.

5. The method of claim 1, wherein the time stamp information is generated using a time reference which delivers Coordinated Universal Time information, in particular one of a radio-controlled clock, a time server, a wide area network time, local area network time, mobile communication network, and a Global Positioning Service device.

6. The method of claim 1, wherein at least one physiologic signal represents at least one value of a parameter, the parameter being one of pH, blood glucose, EMG, heart rate, skin conductivity, body movement, blood pressure, geolocal position, temperature, lightening level, concentrations of biomolecules, noise, and sound.

7. The method of claim 1, wherein at least one data stream is sensed by at least one body-external sensor device.

8. The method of claim 1, wherein the delay is derived from a predetermined probability distribution of delays between the actual happening of the event and the time when the time stamp is recorded.

9. The method of claim 1, wherein the transmitted data streams are encrypted.

10. The method of claim 1, wherein the recorded at least one data stream, the time stamp information, and the associated time shift information relate to a neuroprosthetic device of the patient, and are used for adaptation of at least one parameter of a neuroprosthetic device of the patient, the adaptation being performed in a patient's body-external computer system, and the at least one parameter is transmitted to the neuroprosthetic device via a predetermined communication channel, in particular via a data transmission medium.

11. A non-transitory computer-readable storage medium comprising program code, the program code containing instructions for performing a method according to claim 1, when loaded into a computer system.

12. The method of claim 1, wherein the time shift information is additionally representative of a delay between the point in time of associating the time stamp information and a point in time of recording the data stream by the body-external, portable processing device.

* * * * *